United States Patent [19]

Smith

[11] Patent Number: 5,106,378
[45] Date of Patent: Apr. 21, 1992

[54] ISOLATING COVER FOR A HYPODERMIC NEEDLE

[76] Inventor: Clive G. Smith, 369 Hill St., San Francisco, Calif. 94114

[21] Appl. No.: 572,767

[22] Filed: Aug. 27, 1990

[51] Int. Cl.⁵ .............................................. A61M 5/32
[52] U.S. Cl. ................................................... 604/198
[58] Field of Search ............... 604/198, 110, 162, 167, 604/192, 263

[56] References Cited

U.S. PATENT DOCUMENTS

| | | | |
|---|---|---|---|
| 3,073,306 | 1/1963 | Linder | 604/198 |
| 3,128,920 | 4/1964 | Volckening et al. | 604/192 |
| 3,192,925 | 7/1965 | Cunningham | 604/192 |
| 4,258,713 | 3/1981 | Wardlow | 604/198 |
| 4,425,120 | 1/1983 | Sampson et al. | 604/198 |
| 4,693,708 | 9/1987 | Wanderer et al. | 604/198 |
| 4,702,738 | 12/1987 | Spencer | 604/198 |
| 4,738,663 | 6/1988 | Bogan | 604/198 |
| 4,755,170 | 7/1988 | Golden | 604/198 |
| 4,801,295 | 1/1989 | Spencer | 604/198 |
| 4,850,976 | 7/1989 | Heinrich et al. | 604/192 |
| 4,874,383 | 10/1989 | McNaughton | 604/198 |
| 4,883,470 | 11/1989 | Haindl | 604/263 |
| 4,923,446 | 2/1990 | Page et al. | 604/198 |
| 4,932,940 | 6/1990 | Walker et al. | 604/198 |
| 4,935,011 | 6/1990 | Hogan | 604/263 |

FOREIGN PATENT DOCUMENTS 9000073  1/1990  World Int. Prop. O. ......... 604/198

Primary Examiner—C. Fred Rosenbaum
Assistant Examiner—Sharon Finkel

[57] ABSTRACT

The disclosed invention comprises a transparent sleeve dimensioned to coaxially receive and substantially ensheath the barrel of a disposable type syringe, there being just sufficient clearance between the two to permit easy relative movement. Said sleeve means having a spiked member near one end, which overrides the syringe barrel and rests near the finger plate end of the syringe, the opposite end of the sleeve has a flexibly attached end cap which is enterable thereto.

The sleeve may be moved to cover a hypodermic needle attached to a syringe contained therein, portions of the sleeve and syringe remain correspondent, and are interlocked when the spiked member of the sleeve is caused to penetrate the syringe barrel. The end cap of the sleeve may be entered thereto, further isolating the hypodermic needle.

6 Claims, 2 Drawing Sheets

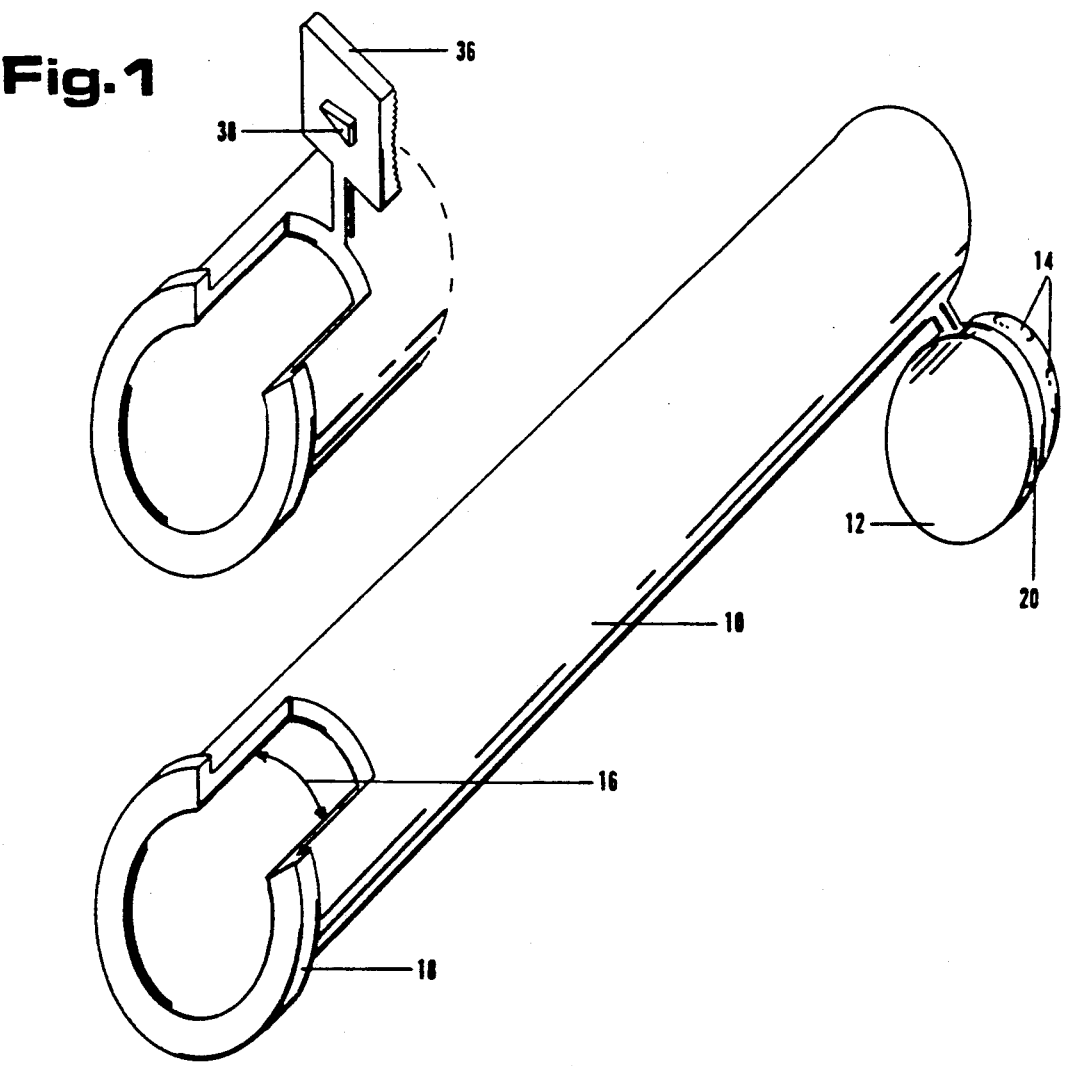
Fig.1
Fig.2
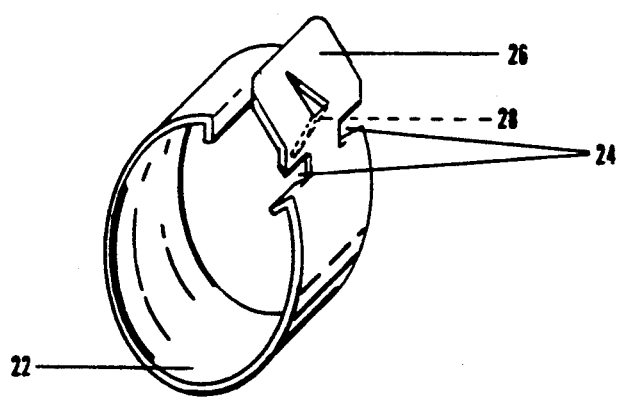
Fig.2a

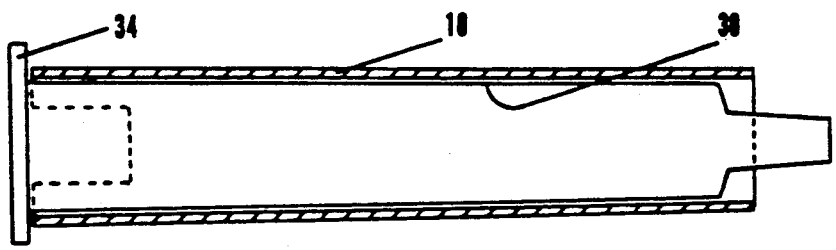
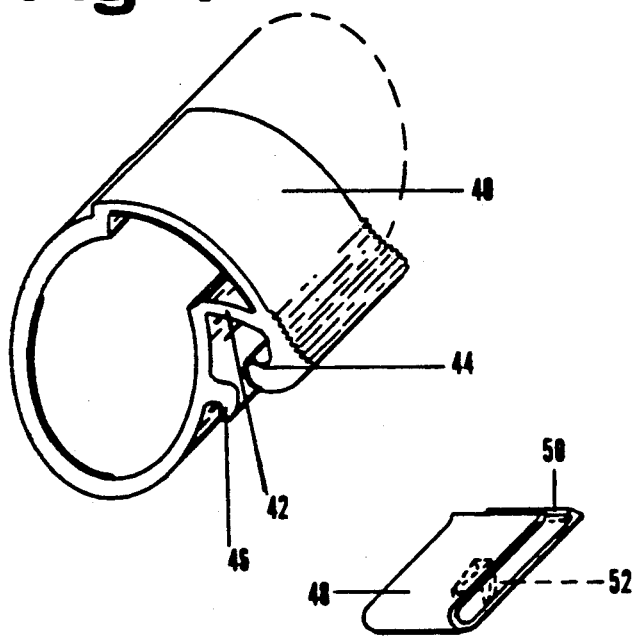
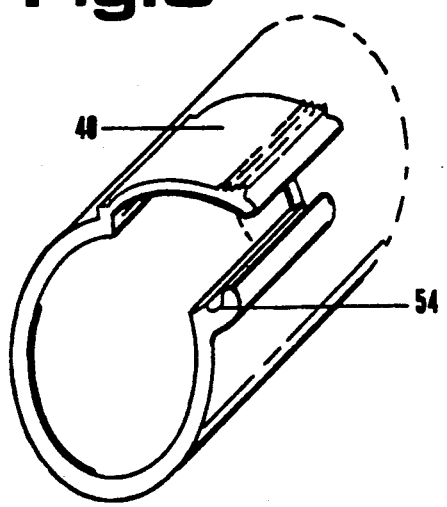
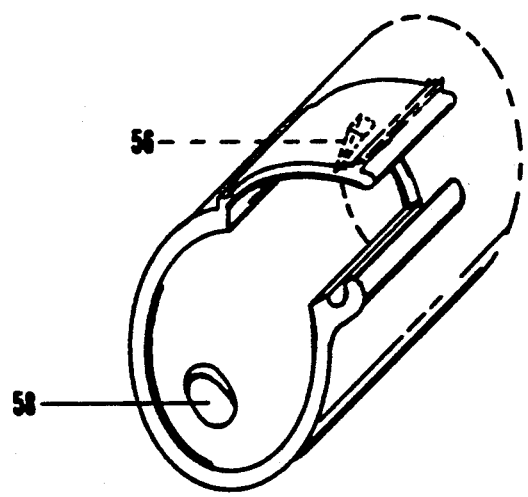

ISOLATING COVER FOR A HYPODERMIC NEEDLE

FIELD OF INVENTION

This invention relates to disposable hypodermic syringes and other hypodermic needle using apparatus.

DISCUSSION OF PRIOR ART

The dangers to medical personnel from contaminated hypodermic needles are well known and much addressed in the art. Known designs toward solving this problem, whilst generally being practical do not lend themselves to economic mass production.

Mostly the approach has been to design entirely new and somewhat complex injection apparatus which often seem to ignore the essentials of very high volume economic production. Generally a plastic molding must have draft in order to facilitate ejection from the mold. Plastic syringe barrels are tapered, whereas the art under discussion shows absolutely cylindrical components, in fact their functioning depends on such.

Most of the art depends upon syringe barrel and sleeve components with various cooperating slots and addendums which would require thick cylinder walls and a commensurate increase in material usage. Also these varying cross sections in a syringe barrel can cause distortion and sinking in the cooling molding, which is problematic since the inside of the barrel must be uniformly round and smooth.

To avoid massive retooling costs it is far more appropriate to design an accessory to currently manufactured hypodermic needle using apparatus.

OBJECTS AND ADVANTAGES

Accordingly an object of this invention is to minimize the incidence of persons being scratched or stuck by contaminated hypodermic needles, in a manner which is economically viable.

Since a major obstacle to acceptance of the art in this field by manufacturers and consumers appears to be economic, the simplicity of this invention and its being entirely adaptable to pre-existing standard disposable syringes is a distinct advantage.

Considering the need for very high volume production and the economy of low maintenance simple molding techniques, the prior art is at a significant disadvantage. being based upon absolutely cylindrical barrel and sleeve components with various cooperating slots and addendum. The general wall thickness in prior art moldings and varying cross sections may cause localized sinking and distortion during cooling, which would be problematic since the inside of a syringe barrel must be uniformly round and smooth.

It is a further advantage of this invention that the barrel of a syringe may be punctured during operation of said invention, thereby rendering the syringe useless in the event of unauthorized salvage.

Further objects and advantages of my invention will become apparent from a consideration of the drawings and ensuing description of it.

DESCRIPTION OF DRAWINGS

FIG. 1 shows an isometric view of the wide end of the sleeve embodying a spike member depressor 36.

FIG. 2 is an exploded isometric view of the sleeve 10 and spike means 22.

FIG. 3 is a side view showing sleeve ensheathing syringe barrel.

FIG. 4 is an isometric view of the wide end of the sleeve embodiment having a sleeve constricting lockable, spike carrying member 40.

FIG. 5 is an isometric view of the wide end of the sleeve embodiment having a lockable spike carrying member 40.

FIG. 6 is an isometric view of the spike clip 48.

FIG. 7 is an isometric view of the wide end of the sleeve embodiment having an integral spike 56.

LIST OF REFERENCE NUMERALS

10: Sleeve
12: End cap
14: Nubs
16: Gap
18: Shoulder
20: End cap shoulder
22: Spike means
24: Notches
26: Spike member
28: Spike
30: Syringe barrel
34: Syringe finger plate
36: Spike member depressor
38: Central protuberance
40: Spike or adhesive carrying member
42: Toggle member
44: Lateral hook
46: Longitudinal hook protuberance
48: Spike clip
50: Retaining lip
52: Spike
54: Rounded groove
56: Integral spike
58: Spike molding member access hole

DESCRIPTION OF INVENTION

The sleeve 10 of FIG. 2 is molded of transparent plastic by conventional method and is necessarily tapered to provide the draft required for easy ejection from the mold, thereby defining a wide end and a narrow end.

Referring to FIG. 3, sleeve 32 is dimensioned to coaxially receive and ensheath the barrel of a disposable plastic syringe 30, there being just sufficient clearance between the two to permit easy relative movement thereof.

Referring to FIG. 2, the narrow end of the sleeve 10 has an adjacent flexibly attached end cap 12. A portion of this end cap 12 which will enter the narrow end of the sleeve 10, has shallow circumferential nubs 14 to engage within a shallow circumferential groove inside said narrow end of said sleeve 10. The extent to which the end cap 12 may enter said sleeve is dictated by a circumferential shoulder 20 on said end cap 12.

The wide end of the sleeve 10 has a peripheral outward extending shoulder 18 for much of the circumference, it being interrupted by a gap 16 which extends toward the narrow end for as far as the spike means 22 is wide.

The spike means 22 is stamped from thin gauge metal and is formed to mostly encircle the wide end of the sleeve 10, said gap 16 not being included, and said spike means 22 abutting said shoulder 18.

Looking at the wide end of the sleeve 10, one end of the spike means 22 band is bent inwardly, to parallel and abutt the left side of the gap 16. Where the spike means 22 band would traverse the right side of the gap 16 it is notched 24 on both sides, the metal displaced by notching remaining in the foregoing length of band and being bent inwardly to parallel and abutt the right side of the gap 16. The further length in the spike means 22 band extends tangentally, flying above the gap 16, this extension is the spike member 26 and has a spike 28 punched out to extend inwardly and central in the gap 16.

The wide end embodiment of FIG. 1 shows a spike member depressor 36, radially disposed on a flexible extension from the centre of the closed end of the gap 16, flat in the plane transverse to the long axis of the sleeve. The face of the spike member depressor 36 toward the wide end has a central protuberance 38 to fit within the punch out for the spike 28 FIG. 2 of the spike member 26 FIG. 2, the opposite face is striated and slightly concave.

The wide end embodiment of FIG. 4 has a gap similar to gap 16 of sleeve 10 FIG. 2 and no shoulder 18 FIG. 2. Looking at the wide end the left side of the gap extends radially outward slightly, thence extends tangentally and clockwise, becoming arcuate, flying above and extending some small distance beyond the gap, therein defining the spike carrying member 40. A toggle member 42 extends outwardly from the right side of the gap and with a clockwise inclination and joins with the spike carrying member 40. The leading edge of the spike carrying member 40 extends radially inward and immediately rolls toward the toggle member 42, forming a lateral hook 44 which is engageable by mutual reciprocatory displacement, within a similar hook, a longitudinal hook protuberance 46 on the sleeve.

The spike clip 48 FIG. 6 is made from a thin gauge metal. One end of a strip is bent through an angle greater than ninety degrees thereby creating the retaining lip 50, the other end is slightly curved in the opposite direction. The strip is folded, bringing the curved end to parallel and nearly meet the retaining lip 50 which is inclined toward the space contained thereby. The side of the spike clip 48 which has the retiaining lip 50 has a spike 52 punched therefrom which extends outwardly.

This spike clip 48 is slidably installed over that section of the spike carrying member 40 which is over the gap in the wide end of the sleeve.

The wide end embodiment of FIG. 5 has a gap similar to gap 16 of sleeve 10 FIG. 2 and no shoulder 18 FIG. 2. Looking at the wide end the left side of the gap extends radially outward slightly, thence extends tangentally and clockwise, becoming arcuate, flying above and extending some slight distance beyond the right side of the gap, therein defining the spike carrying member 40 of this embodiment. The leading edge of this spike carrying member 40 is rounded, to be engageable by mutual reciprocatory displacement within a rounded groove in the length of a radially outward extension of the right side of the gap.

The previously described spike clip 48 slidably installs over this spike carrying member 40.

The wide end embodiment of FIG. 7 is substantially the same as that of FIG. 5. Instead of installing a separate spike the spike 56 is an integral part of the molding. There is a spike molding member access hole 58 in the sleeve and opposite the spike, centred in the long axis of the spike 56.

OPERATION

When the syringe barrel is fully inserted into the sleeve the syringe remains fully and normally functional. After an injection has been administered the sleeve may be held to the patient whilst the syringe and accompanying needle are withdrawn from the sleeve just sufficiently that the needle is ensheathed by the sleeve.

To lock the sleeve of FIG. 2 to the syringe, spike member 26 is depressed to cause the spike 28 to penetrate the syringe barrel, thereby interlocking the sleeve and syinge barrel. FIG. 1 shows a spike member depressor 36 which has a greater surface area than the spike member 26, whereby less force is required to depress the spike member 26.

To lock the sleeve of FIG. 4 pressure is applied to the spike carrying member 40. Counter acting torsional forces on the sides of the gap constrict this end of the sleeve against the syringe barrel whilst the spike 52 FIG. 6 is caused to penetrate the syringe barrel, thereby interlocking the sleeve and syringe barrel. Finally, the lateral hook 44 of the leading edge of the spike carrying member 40 is caused to engage within the longitudinal hook protuberance 46 of the sleeve by mutual reciprocatory displacement.

To lock the sleeve of FIG. 5 pressure is applied to the spike carrying member 40. The spike 52 FIG. 6 is caused to penetrate the syringe barrel, thereby interlocking the sleeve and syringe barrel. Finally the rounded leading edge of the spike carrying member 40 is caused to engage within the rounded groove 54 of the sleeve by mutual reciprocatory displacement.

Operation of the sleeve in FIG. 7 is the same as that for the preceding sleeve of FIG. 5, the spike in this case being integral spike 56.

In all of the above sleeve operations, a final safety feature is to enter the sleeve end cap 12 FIG. 2 into the sleeve.

From the foregoing description of this invention one may appreciate that this simple, economic, easy to use device might save health workers from much grief and anxiety. A preferred embodiment would be one which is efficient and economic of manufacture, most likely one wherein the spike is an integral part of the molding.

While the above description contains many specificities, these should not be construed as limitations on the scope of the invention, but rather as exemplification of preferred embodiments thereof. Many possible variations include the following.

The constricting action of the sleeve in FIG. 4 could be enhanced by slots in the sleeve, extending from the ends of the end line in the gap circumferentially or less effectively, longitudinally.

When the spike is punched from metal its base may be in the long axis of the sleeve or transverse.

The spike clip FIG. 6 may be molded from plastic.

Extra spikes punched in the band of the spike means FIG. 2 may be used to staple the spike means to the sleeve, whereby a straight cylindrical sleeve with no shoulder could be employed.

The spike may be intended to penetrate the sleeve and the syringe barrel, whereby no gap in the sleeve wherethrough the spike may pass is necessary.

The syringe barrel engaging means of the sleeve may have one or many spikes or protuberances, to penetrate or just engage the syringe barrel.

A spike means may be inserted into the mold, whereby it will be integrated into the molding of the sleeve.

The spike may be barbed.

The sleeve taper may be such as to frictionally engage one end or the other of the syringe barrel when the syringe is fully entered thereto.

The sleeve may have a finger plate at its wide end, as does the syringe.

The syringe barrel engaging means may be adhesive or frictional.

The narrow end of the sleeve may be totally closed, to be penetrated by the needle as the syringe is inserted, or it may be open by any increment.

The sleeve may be non-transparent, with or without a means whereby fluid content of the syringe may be determined.

The principles embodied in this invention are well suited to other hypodermic devices. Accordingly, the scope of my invention should be determined not by the embodiments illustrated but by the following claims and their legal equivalents.

What I claim is:

1. An isolating cover for a hypodermic needle comprising: a sleeve to coaxially ensheath a plastic hypodermic syringe barrel, said sleeve is axially and forwardly deployable to cover a hypodermic needle attached to said syringe barrel, and long enough that when deployed to cover the needle, a rearmost portion of said sleeve remains around a forward end portion of said syringe barrel; said rearmost portion of said sleeve has a spike means attached to it, said spike means incorporates a spike member having a spike angled inwardly toward said syringe barrel, said spike member is depressable inwardly to cause said spike to penetrate said syringe barrel, thereby interlocking said sleeve with said syringe barrel, whereby the hypodermic needle is safely covered and the punctured syringe barrel is rendered useless.

2. An isolating cover for a hypodermic needle comprising: a plastic sleeve to coaxially ensheath a plastic hypodermic syringe barrel, said sleeve is axially and forwardly deployable to cover a hypodermic needle attached to said syringe barrel, and long enough that when deployed to cover the needle, a rearmost portion of said sleeve remains around a forward end portion of said syringe barrel; the circumference of said rearmost portion of said sleeve has a longitudinal gap, which is bridged by an integrally molded member hingably attached to one longitudinal side of said gap, and attached by a toggle member to the other side of said gap and adapted to be lockably engagable with an integrally molded latch in said rearmost portion of said sleeve, whereby inward depression of the member which bridges said longitudinal gap causes counter torsional forces which reduce the width of the gap and lockably constrict said rearmost portion of said sleeve around said forward end portion of said syringe barrel, whereby the hypodermic needle is safely covered.

3. The invention of claim 2 wherein the inner surface of the member which bridges said longitudinal gap has an adhesive material applied thereto, to adhesively engage said forward end portion of said syringe barrel when the member is inwardly depressed.

4. The invention of claim 2 wherein the member which bridges said longitudinal gap has an inwardly angled spike means, to engage said forward end of said syringe barrel when the member is inwardly depressed.

5. An isolating cover for a hypodermic needle comprising: a plastic sleeve to coaxially ensheath a plastic hypodermic syringe barrel, said sleeve is axially and forwardly deployable to cover a hypodermic needle attached to said syringe barrel, and long enough that when deployed to cover the needle, a rear-most portion of said sleeve remains around a forward end portion of said syringe barrel; the circumference of said rear most portion of said sleeve has a longitudinal gap, hingably attached to one longitudinal side of said gap is a member which extends angularly outward accross said gap and is adapted to be lockably engagable with an integrally molded latch in said rearmost portion of said sleeve; the inner surface of the member accross the gap has an adhesive material applied thereto, whereby inward depression of the member causes lockable adhesive attachment of said sleeve to said syringe barrel, thereby safely covering the hypodermic needle.

6. The invention of claim 5 wherein the member accross the gap has an inwardly angled spike means, to engage said forward end of said syringe barrel when the member is inwardly depressed.

* * * * *